(12) United States Patent
Simpson et al.

(10) Patent No.: US 11,653,672 B2
(45) Date of Patent: May 23, 2023

(54) GAS FERMENTATION FOR THE PRODUCTION OF PROTEIN OR FEED

(71) Applicant: LanzaTech NZ, Inc., Skokie, IL (US)

(72) Inventors: Sean Simpson, Evanston, IL (US);
Wyatt Eric Allen, Chicago, IL (US);
Robert John Conrado, Washington, DC (US); Sean Molloy, Auckland (NZ)

(73) Assignee: LanzaTech NZ, Inc., Skokie, IL (US)

( * ) Notice: Subject to any disclaimer, the term of this patent is extended or adjusted under 35 U.S.C. 154(b) by 207 days.

(21) Appl. No.: 17/100,640

(22) Filed: Nov. 20, 2020

(65) Prior Publication Data

US 2021/0084933 A1   Mar. 25, 2021

Related U.S. Application Data

(63) Continuation of application No. 15/159,479, filed on May 19, 2016, now Pat. No. 10,856,560.

(60) Provisional application No. 62/165,182, filed on May 21, 2015.

(51) Int. Cl.
| | | |
|---|---|---|
| *A23K 10/12* | (2016.01) | |
| *C12N 1/20* | (2006.01) | |
| *A23K 50/10* | (2016.01) | |
| *A23K 50/40* | (2016.01) | |
| *A23K 50/30* | (2016.01) | |

(52) U.S. Cl.
CPC ............. *A23K 10/12* (2016.05); *A23K 50/10* (2016.05); *A23K 50/30* (2016.05); *A23K 50/40* (2016.05); *C12N 1/20* (2013.01)

(58) Field of Classification Search
CPC .......... A23K 10/12; A23K 5/10; A23K 50/30; A23K 50/40; C12N 1/20

USPC ............................................... 426/61
See application file for complete search history.

(56) References Cited

U.S. PATENT DOCUMENTS

| | | | | |
|---|---|---|---|---|
| 3,887,431 A | * | 6/1975 | Robbins | C12N 1/005 435/270 |
| 5,807,722 A | * | 9/1998 | Gaddy | C12M 29/04 435/163 |
| 2006/0051323 A1 | * | 3/2006 | Bijl | A23P 10/30 514/52 |
| 2013/0316412 A1 | * | 11/2013 | Schultz | C12P 7/06 435/150 |
| 2014/0013658 A1 | * | 1/2014 | Silverman | C12N 15/52 435/167 |

FOREIGN PATENT DOCUMENTS

JP     2007082438 A     4/2007

OTHER PUBLICATIONS

CN109007257—English Abstract (Year: 2018).*
Daramwal et al. (Year: 2004).*
Notice of Reasons for Refusal issued in corresponding Japanese Application No. 2017-560620, dated Dec. 1, 2020, 8 pages.

* cited by examiner

*Primary Examiner* — Hamid R Badr
(74) *Attorney, Agent, or Firm* — Frank S. Molinaro

(57) ABSTRACT

The invention provides animal feed comprising microbial biomass and methods of producing animal feed by culturing a microorganism to produce microbial biomass. In particular, the invention relates to animal feed produced by fermentation of a gaseous substrate comprising one or more of CO, $CO_2$, and $H_2$, especially by a Gram-positive, anaerobic, and/or *Clostridium* microorganism.

16 Claims, No Drawings

GAS FERMENTATION FOR THE PRODUCTION OF PROTEIN OR FEED

CROSS REFERENCE TO RELATED APPLICATIONS

This application is a continuation of U.S. patent application Ser. No. 15/159,479 filed May 19, 2016, which claims the benefit of U.S. Provisional Application No. 62/165,182 filed May 21, 2015, the entireties of which are incorporated herein by reference.

BACKGROUND OF THE INVENTION

Single cell protein (SCP) refers to microbial biomass for use in protein-rich human and animal feeds, often replacing conventional sources of protein supplementation such as soymeal or fishmeal.

Large-scale production of microbial biomass has many advantages over traditional methods for producing proteins for food or feed. For example, microorganisms have high growth rates, can be genetically modified to tailor amino acid composition, have high protein content, and can utilize a broad spectrum of carbon and energy sources. Moreover, bioconversion of agricultural and industrial wastes to protein-rich feed stocks has an additional benefit of making the final product cheaper, which also offsets the negative cost value of wastes used as substrate to yield SCP. Further, use of SCP renders feed production less dependent upon land resources and relieves pressure on agriculture.

Algae, fungi, and bacteria are the chief sources of SCP (Ravindra, *Biotechnol Adv*, 18: 459-479, 2000). Bacterial species previously used for SCP include *Methylophilus methylotrophicus* (Imperial Chemical Industries), *Methylophilus clara* (Hoechst), and *Methylophilus methanica* (Norsk Hydro). However, each of these microorganisms are Gram-negative and aerobic and consume methanol as a carbon source. Accordingly, there remains a need for additional animal feeds comprising microbial biomass from different strains and grown on different carbon sources.

SUMMARY OF THE INVENTION

The invention provides animal feed comprising microbial biomass and at least one excipient. Generally, the microbial biomass comprises a microorganism grown on a gaseous substrate, such as a gaseous substrate comprising one or more of CO, $CO_2$, and $H_2$.

The microorganism may be Gram-positive, acetogenic, carboxydotrophic, and/or anaerobic. Generally, the microorganism is a member of the genus *Clostridium*, such as a microorganism that is or is derived from *Clostridium autoethanogenum*, *Clostridium ljungdahlii*, *Clostridium ragsdalei*, or *Clostridium coskatii*. In a preferred embodiment, the microorganism is *Clostridium autoethanogenum* deposited under DSMZ accession number DSM23693. In certain embodiments, the microorganism is not methanotrophic.

The gaseous substrate comprises one or more of CO, $CO_2$, and $H_2$. Typically, the gaseous substrate comprises at least some amount of CO. In certain embodiments, the gaseous substrate does not comprise methane. However, in particular embodiments, the gaseous substrate may be generated via methane reforming. The gaseous substrate may be or may be derived from an industrial waste gas, an industrial off gas, or syngas.

The animal feed is suitable for feeding to livestock or pets, including, but not limited to, beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents.

The animal feed may further comprise one or more excipients, such as a carbohydrate, fiber, fat, protein, vitamin, mineral, water, flavor, sweetener, antioxidant, enzyme, preservative, probiotic, or antibiotic. More generally, the excipient may be any substance added to the microbial biomass to enhance or alter the form, properties, or nutritional content of the animal feed.

The invention further provides a method for producing the animal feed comprising culturing a microorganism in the presence of a gaseous substrate to form microbial biomass and producing animal feed from the microbial biomass. Generally, the gaseous substrate comprises one or more of CO, $CO_2$, and $H_2$.

The method may comprise additional steps. For example, the method may comprise a step of reducing the nucleic acid content of the microbial biomass. The method may also comprise one or more steps of sterilizing the microbial biomass, centrifuging the microbial biomass, and drying the microbial biomass. In particular, the drying may be spray drying or paddle drying. Furthermore, the method may comprise blending the microbial biomass with the excipient. The method may also comprise culturing the microorganism under fermentation conditions that maximize production of microbial biomass.

DETAILED DESCRIPTION OF THE INVENTION

The inventors have discovered that microbial biomass produced from the fermentation of gaseous substrates, particularly gaseous substrates comprising one or more of CO, $CO_2$, and $H_2$, is particularly suitable source of SCP for use in animal feed.

The invention provides animal feed comprising microbial biomass and at least one excipient, wherein the microbial biomass comprises a microorganism grown on a gaseous substrate, such as a gaseous substrate comprising one or more of CO, $CO_2$, and $H_2$.

A "microorganism" or "microbe" is a microscopic organism, especially a bacterium, archaea, virus, or fungus. The microorganism is typically a bacterium. As used herein, recitation of "microorganism" should be taken to encompass "bacterium."

"Microbial biomass" refers biological material comprising microorganism cells. For example, microbial biomass may comprise or consist of a pure or substantially pure culture of a bacterium, archaea, virus, or fungus. When initially separated from a fermentation broth, microbial biomass generally contains a large amount of water. This water may be removed or reduced by drying or processing the microbial biomass.

The microbial biomass may comprise any of the components listed in the first column of the table in Example 1. Notably, the microbial biomass of Example 1 comprises 15% moisture (water) by weight. Accordingly, the values listed in Example 1 refer to amounts of each component per amount of wet (i.e., non-dried) microbial biomass. Herein, the composition of the microbial biomass is described in terms of weight of a component per weight of wet (i.e., non-dried) microbial biomass. Of course, it is also possible to calculate the composition of the microbial biomass in terms of weight of a component per weight of dry microbial biomass.

The microbial biomass generally contains a large fraction of protein, such as more than 50% (50 g protein/100 g biomass), more than 60% (60 g protein/100 g biomass), The microorganism may classified based on functional characteristics. For example, the microorganism may be or may be derived from a C1-fixing microorganism, an anaerobe, an acetogen, an ethanologen, and/or a carboxydotroph. Table 1 provides a representative list of microorganisms and identifies their functional characteristics.

TABLE 1

| | C1-fixing | Anaerobe | Acetogen | Ethanologen | Autotroph | Carboxydotroph | Methanotroph |
|---|---|---|---|---|---|---|---|
| *Acetobacterium woodii* | + | + | + | +/−[1] | − | +/−[2] | − |
| *Alkalibaculum bacchii* | + | + | + | + | + | + | − |
| *Blautia producta* | + | + | + | − | + | + | − |
| *Butyribacterium methylotrophicum* | + | + | + | + | + | + | − |
| *Clostridium aceticum* | + | + | + | − | + | + | − |
| *Clostridium autoethanogenum* | + | + | + | + | + | + | − |
| *Clostridium carboxidivorans* | + | + | + | + | + | + | − |
| *Clostridium coskatii* | + | + | + | + | + | + | − |
| *Clostridium drakei* | + | + | + | − | + | + | − |
| *Clostridium formicoaceticum* | + | + | + | − | + | + | − |
| *Clostridium ljungdahlii* | + | + | + | + | + | + | − |
| *Clostridium magnum* | + | + | + | − | + | +/−[3] | − |
| *Clostridium ragsdalei* | + | + | + | + | + | + | − |
| *Clostridium scatologenes* | + | + | + | − | + | + | − |
| *Eubacterium limosum* | + | + | + | − | + | + | − |
| *Moorella thermautotrophica* | + | + | + | + | + | + | − |
| *Moorella thermoacetica* (formerly *Clostridium thermoaceticum*) | + | + | + | −[4] | + | + | − |
| *Oxobacter pfennigii* | + | + | + | − | + | + | − |
| *Sporomusa ovata* | + | + | + | − | + | +/−[5] | − |
| *Sporomusa silvacetica* | + | + | + | − | + | +/−[6] | − |
| *Sporomusa sphaeroides* | + | + | + | − | + | +/−[7] | − |
| *Thermoanaerobacter kivui* | + | + | + | − | + | − | − |

[1]*Acetobacterium woodii* can produce ethanol from fructose, but not from gas.
[2]It has been reported *Acetobacterium woodii* can grow on CO, but the methodology is questionable.
[3]It has not been investigated whether *Clostridium magnum* can grow on CO.
[4]One strain of *Moorella thermoacetica*, *Moorella* sp. HUC22-1, has been reported to produce ethanol from gas.
[5]It has not been investigated whether *Sporomusa ovata* can grow on CO.
[6]It has not been investigated whether *Sporomusa silvacetica* can grow on CO.
[7]It has not been investigated whether *Sporomusa sphaeroides* can grow on CO.

more than 70% (70 g protein/100 g biomass), or more than 80% (80 g protein/100 g biomass) protein by weight. In a preferred embodiment, the microbial biomass comprises at least 72% (72 g protein/100 g biomass) protein by weight. The protein fraction comprises amino acids, including aspartic acid, alanine, arginine, cysteine, glutamic acid, glycine, histidine, isoleucine, leucine, lysine, methionine, phenylalanine, proline, serine, threonine, tyrosine, and/or valine. In particular, the microbial biomass may comprise more than 10 mg methionine/g biomass, more than 15 mg methionine/g biomass, more than 20 mg methionine/g biomass, or more than 25 mg methionine/g biomass. In a preferred embodiment, the microbial biomass comprises at least 17.6 mg methionine/g biomass.

The microbial biomass may contain a number of vitamins, including vitamins A (retinol), C, B1 (thiamine), B2 (riboflavin), B3 (niacin), B5 (pantothenic acid), and/or B6 (pyridoxine).

The microbial biomass may contain relatively small amounts of carbohydrates and fats. For example, the microbial biomass may comprise less than 15% (15 g carbohydrate/100 g biomass), less than 10% (10 g carbohydrate/100 g biomass), or less than 5% (5 g carbohydrate/100 g biomass) of carbohydrate by weight. For example, the microbial biomass may comprise less than 10% (10 g fat/100 g biomass), or less than 5% (5 g fat/100 g biomass), less than 2% (2 g fat/100 g biomass), or less than 1% (1 g fat/100 g biomass) of fat by weight.

"C1" refers to a one-carbon molecule, for example, CO or $CO_2$. "C1-oxygenate" refers to a one-carbon molecule that also comprises at least one oxygen atom, for example, CO or $CO_2$. "C1-carbon source" refers a one carbon-molecule that serves as a partial or sole carbon source for the microorganism. For example, a C1-carbon source may comprise one or more of CO, $CO_2$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism is a C1-fixing bacterium. In a preferred embodiment, the microorganism is or is derived from a C1-fixing microorganism identified in Table 1.

An "anaerobe" is a microorganism that does not require oxygen for growth. An anaerobe may react negatively or even die if oxygen is present above a certain threshold. Typically, the microorganism is an anaerobe (i.e., is anaerobic). In a preferred embodiment, the microorganism is or is derived from an anaerobe identified in Table 1.

An "acetogen" is a microorganism that produces or is capable of producing acetate (or acetic acid) as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). Acetogens use the acetyl-CoA pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, N.Y., 2006). All naturally occurring acetogens are C1-fixing, anaerobic, autotrophic, and non-methanotrophic. In a preferred embodiment, the microorganism is an acetogen. In a preferred embodiment, the microorganism is or is derived from an acetogen identified in Table 1.

An "ethanologen" is a microorganism that produces or is capable of producing ethanol. In a preferred embodiment, the microorganism is an ethanologen. In a preferred embodiment, the microorganism is or is derived from an ethanologen identified in Table 1.

An "autotroph" is a microorganism capable of growing in the absence of organic carbon. Instead, autotrophs use inorganic carbon sources, such as CO and/or $CO_2$. In a preferred embodiment, the microorganism is an autotroph. In a preferred embodiment, the microorganism is or is derived from an autotroph identified in Table 1.

A "carboxydotroph" is a microorganism capable of utilizing CO as a sole source of carbon. In a preferred embodiment, the microorganism is a carboxydotroph. In a preferred embodiment, the microorganism is or is derived from a carboxydotroph identified in Table 1.

In certain embodiments, the microorganism does not consume certain substrates, such as methane or methanol. In one embodiment, the microorganism is not a methanotroph and/or is not a methylotroph.

Preferably, the microorganism is Gram-positive. Most prior work on the use of SCP in animal feed involved Gram-negative species, such as *Methylophilus methylotrophicus, Methylophilus clara,* and *Methylophilus methanica*. However, Gram-negative bacteria often produce or contain endotoxins that make their use in animal feed problematic. Because endotoxins are the part of cellular components of some of the Gram-negative bacteria and are not released into the medium by the living bacterial cell, their removal is somewhat difficult. Their formation can only be prevented by genetic engineering, where the activity of genes controlling the formation of the unwanted toxins can be modified or suppressed. This may be a difficult task to achieve, as they are integral structural components of the bacterial cell wall (Ravindra, *Biotechnol Adv,* 18: 459-479, 2000).

More broadly, the microorganism may be or may be derived from any genus or species identified in Table 1. For example, the microorganism may be a member of the genus *Clostridium*.

In a preferred embodiment, the microorganism is or is derived from the cluster of Clostridia comprising the species *Clostridium autoethanogenum, Clostridium ljungdahlii,* and *Clostridium ragsdalei*. These species were first reported and characterized by Abrini, *Arch Microbiol,* 161: 345-351, 1994 (*Clostridium autoethanogenum*), Tanner, *Int J System Bacteriol,* 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 μm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng,* 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Kopke, *Curr Opin Biotechnol,* 22: 320-325, 2011).

Thus, in summary, many of the characteristics of *Clostridium autoethanogenum, Clostridium ljungdahlii,* or *Clostridium ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism may also be or be derived from an isolate or mutant of *Clostridium autoethanogenum, Clostridium ljungdahlii,* or *Clostridium ragsdalei*. Isolates and mutants of *Clostridium autoethanogenum* include JA1-1 (DSM10061) (Abrini, *Arch Microbiol,* 161: 345-351, 1994), LBS1560 (DSM19630) (WO 2009/064200), and LZ1561 (DSM23693). Isolates and mutants of *Clostridium ljungdahlii* include ATCC 49587 (Tanner, *Int J Syst Bacteriol,* 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

The term "derived from" refers to a microorganism is modified or adapted from a different (e.g., a parental or wild-type) microorganism, so as to produce a new microorganism. Such modifications or adaptations typically include insertion, deletion, mutation, or substitution of nucleic acids or genes.

"Substrate" refers to a carbon and/or energy source for the microorganism. Typically, the substrate is gaseous and comprises a C1-carbon source, for example, CO or $CO_2$. Preferably, the substrate comprises a C1-carbon source of CO or $CO+CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism typically converts at least a portion of the CO and/or in the substrate to a product. In some embodiments, the substrate comprises no or substantially no CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no $CO_2$.

In some embodiments, the substrate does not comprise methane or methanol.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be or may be derived from a waste or off gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be or may be derived from syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

In connection with substrates and/or C1-carbon sources, the term "derived from" refers to a substrate and/or C1-carbon source that is somehow modified or blended. For example, the substrate and/or C1-carbon source may be treated to add or remove certain components or may be blended with streams of other substrates and/or C1-carbon sources.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The invention further provides a method for producing animal feed, comprising culturing a microorganism in the presence of a gaseous substrate comprising one or more of CO, $CO_2$, and $H_2$ to form microbial biomass and producing animal feed from the microbial biomass.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Herein, microbial biomass itself is considered a target product. However, the microorganism also produce one or more other products of value. For instance, *Clostridium autoethanogenum* produces or can be engineered to produce ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/0369152), and 1-propanol (WO 2014/0369152).

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

The culturing of the microorganism may be performed under fermentation conditions that maximize production of microbial biomass. The method may also comprise culturing the microorganism under fermentation conditions that maximize production of or selectivity to microbial biomass. Maximizing selectivity to biomass requires operation at maximal specific growth rates or maximal microorganism dilution rate. However, operation at high microorganism dilution rates also reduces the cell concentration in the culture which hampers separations. Also, cell concentration is a key requirement for high reactor productivity. Specific growth rates or microorganism dilution rates of >1/day should be targeted, with rates of 2/day being closer to the optimum.

In a two reactor system, biomass production rates are maximized by having high biomass production rates in both the first and second reactor. This can be achieved by either having (1) low cell viability or (2) fast specific growth rates in the second reactor. Low cell viability may be achieved from the toxicity of high product titers and may not be desirable. Fast specific growth rates may be achieved by operating with even higher values of microorganism dilution rate in the second reactor compared to the first reactor.

This relationship is captured by the following equation: $\mu_2 = D_{w2} - D_{w1} * (X_1/X_2) * (V_1/V_2)$, where $\mu_2$ is the specific growth rate in the second reactor in a two reactor system which will need to be maximized to increase selectivity to biomass, $D_{w2}$ and $D_{w1}$ are the microorganism dilution rates in the second and first reactors in a two reactor system, respectively, $X_2$ and $X_1$ are the biomass titers in the second and first reactors in a two reactor system, respectively, and $V_2$ and $V_1$ are the reactor volumes in the second and first reactors in a two reactor system, respectively.

According to this equation, to maximize the selectivity to biomass in a second reactor, the microorganism dilution rate in the second reactor, $D_{w2}$, will need to be increased to achieve a specific growth rate, $\mu_2$, in the second reactor of >0.5/day, ideally targeting 1-2/day.

Products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Cell-free permeate remaining after products have been removed is also preferably returned to the bioreactor. Additional nutrients (such as B vitamins) may be added to the cell-free permeate to replenish the medium before it is returned to the bioreactor.

The method of the invention may further comprise additional separation, processing, or treatment steps. For example, the method may comprise sterilizing the microbial biomass, centrifuging the microbial biomass, and/or drying the microbial biomass. In certain embodiments, the microbial biomass is dried using spray drying or paddle drying. The method may also comprise reducing the nucleic acid content of the microbial biomass using any method known in the art, since intake of a diet high in nucleic acid content may result in the accumulation of nucleic acid degradation products and/or gastrointestinal distress. Furthermore, the method may comprise blending or combining the microbial biomass with one or more excipients.

The animal feed is suitable for feeding to animals, such as livestock or pets. In particular, the animal feed may be suitable for feeding to one or more of beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents. The composition of the animal feed may be tailored to the nutritional requirements of different animals.

Generally, the animal feed comprises at least one excipient. Herein, "excipient" refers to any substance that may be added to the microbial biomass to enhance or alter the form, properties, or nutritional content of the animal feed. For example, the excipient may comprise one or more of a carbohydrate, fiber, fat, protein, vitamin, mineral, water, flavor, sweetener, antioxidant, enzyme, preservative, probiotic, or antibiotic. In some embodiments, the excipient may be hay, straw, silage, grains, oils or fats, or other plant material.

The excipient may be any feed ingredient identified in Chiba, Section 18: Diet Formulation and Common Feed Ingredients, Animal Nutrition Handbook, $3^{rd}$ revision, pages 575-633, 2014, including alfalfa, animal fat, bakery waste, barley, beet pulp, bermudagrass, blood meal or plasma, brewer's grain, brewer's yeast, bromegrass, buckwheat, canarygrass, canola, casein, citrus pulp, clover, coconut, corn, corn cob, cottonseed, feather meal, fescue, fish meal or solubles, hominy, meat or bone meal, milk, millet, molasses, oats, orchardgrass, peas, peanuts, poultry meal, rice, rye, ryegrass, safflower, sesame, sorghum, soybean, sunflower, timothy, triticale, urea, wheat, whey, or yeast.

EXAMPLES

The following examples further illustrate the invention but, of course, should not be construed to limit its scope in any way.

Example 1

This example describes the composition of *C. autoethanogenum* DSM23693 microbial biomass.

| Component | Result | Unit | Testing Method |
|---|---|---|---|
| Calories (calculation) | 329 | kcal/100 g | 21 CFR Part 101 |
| Calories from fat (calculation) | ND | kcal/100 g | 21 CFR Part 101 |

-continued

| Component | Result | Unit | Testing Method |
| --- | --- | --- | --- |
| Total carbohydrates (calculation) | 10 | g/100 g | 21 CFR Part 101 |
| Vitamin A (retinol) | ND | IU/100 g | AOAC 2001.13 |
| Calcium | 42 | mg/100 g | AOAC 2011.14 |
| Iron | 29 | mg/100 g | AOAC 2011.14 |
| Sodium | 170 | mg/100 g | AOAC 2011.14 |
| Copper | 0.525 | mg/Kg | SW6010C/SW3061 |
| Magnesium | 193 | mg/Kg | SW6010C/SW3065 |
| Manganese | <4.7 | mg/Kg | SW6010C/SW3066 |
| Phosphorus | 6720 | mg/Kg | SW6010C/SW3066 |
| Potassium | 6520 | mg/Kg | SW6010C/SW3066 |
| Selenium | 14.3 | mg/Kg | SW6010C/SW3066 |
| Sodium | 1960 | mg/Kg | SW6010C/SW3066 |
| Zinc | 53 | mg/Kg | SW6010C/SW3066 |
| Ash | 2.6 | g/100 g | AOAC 923.03 |
| Moisture | 15 | g/100 g | AOAC 927.05/950.46 |
| Total sugar | ND | g/100 g | AOAC 982.14 |
| Total dietary fiber | 9.1 | g/100 g | AOAC 2011.25 mod |
| Protein | 72 | g/100 g | AOAC 992.15/992.23 |
| Cholesterol | ND | mg/100 g | AOAC 994.1 |
| Monounsaturated fat | ND | g/100 g | AOAC 996.06 |
| Polyunsaturated fat | ND | g/100 g | AOAC 996.06 |
| Saturated fat | ND | g/100 g | AOAC 996.06 |
| Total fat | ND | g/100 g | AOAC 996.06 |
| Trans fat | ND | g/100 g | AOAC 996.06 |
| Vitamin C | ND | mg/100 g | JAFC (2003) |
| B1 (thiamine) | 0.07 | mg/100 g | Vitamin[1] |
| B2 (riboflavin) | 3.53 | mg/100 g | Vitamin[1] |
| B3 (niacin) | 7.44 | mg/100 g | Vitamin[1] |
| B5 (pantothenic acid) | 0.12 | mg/100 g | Vitamin[1] |
| B6 (pyridoxine) | 0.532 | mg/100 g | Vitamin[1] |
| Total amino acids | | | |
| Aspartic acid | 78.5 | mg/g | Total amino acid[2] |
| Alanine | 44 | mg/g | Total amino acid[2] |
| Arginine | 27.9 | mg/g | Total amino acid[2] |
| Cystine | 6.35 | mg/g | Total amino acid[2] |
| Glutamic acid | 73.4 | mg/g | Total amino acid[2] |
| Glycine | 31.2 | mg/g | Total amino acid[2] |
| Histidine | 10.2 | mg/g | Total amino acid[2] |
| Isoleucine | 43.9 | mg/g | Total amino acid[2] |
| Leucine | 48.7 | mg/g | Total amino acid[2] |
| Lysine | 66.2 | mg/g | Total amino acid[2] |
| Methionine | 17.6 | mg/g | Total amino acid[2] |
| Phenylalanine | 25.8 | mg/g | Total amino acid[2] |
| Proline | 21.7 | mg/g | Total amino acid[2] |
| Serine | 27.8 | mg/g | Total amino acid[2] |
| Threonine | 34.7 | mg/g | Total amino acid[2] |
| Tyrosine | 29.4 | mg/g | Total amino acid[2] |
| Valine | 41.9 | mg/g | Total amino acid[2] |

[1]AOAC 944.13, AOAC 960.46, AOAC 945.74, AOAC 961.15, AOAC 940.33, AOAC 942.23, AOAC 953.17, AOAC 957.17

[2]Methods used: AOAC 944.13, AOAC 960.46, AOAC 945.74, AOAC 961.15, AOAC 940.33, AOAC 942.23, AOAC 953.17, AOAC 957.17, AOAC 988.15, R. Schuster, "Determination of Amino Acids in Biological, Pharmaceutical, Plant and Food Samples by Automated Precolumn Derivatization and HPLC", Journal of Chromatography, 1988, 431, 271-284. Henderson, J. W., Brooks, A., "Improved Amino Acid Methods using Agilent Zorbax Eclipse Plus C18 Columns for a Variety of Agilent LC Instrumentation and Separation Goals," Agilent Application Note 5990-4547 (2010)., Henderson, J. W., Ricker, R. D. Bidlingmeyer, B. A., Woodward, C., "Rapid, Accurate, Sensitive, and Reproducible HPLC Analysis of Amino Acids, Amino Acid Analysis Using Zorbax Eclipse-AAA columns and the Agilent 1100 HPLC," Agilent Publication, 2000.

nt = not tested

ND = not detected (below the detection limit of the method)

< = element not detected; value shown is the limit of detection of the method

Example 2

This example compares the amino acid composition of *C. autoethanogenum* DSM23693 biomass to the amino acid compositions of other types of feed protein supplements.

|  | *C. autoethanogenum* DSM23693 biomass | Soybean Meal * | White Fish Meal* | Herring Type Fish Meal* | Unit |
|---|---|---|---|---|---|
| Alanine | 3.2 | na | na | na | g per 100 g protein |
| Arginine | 2.0 | 3.2 | 4.1 | 4.2 | g per 100 g protein |
| Aspartic acid | 5.7 | na | na | na | g per 100 g protein |
| Cystine | 0.5 | 1.3 | 2.3 | 2.9 | g per 100 g protein |
| Glutamic acid | 5.3 | na | na | na | g per 100 g protein |
| Glycine | 2.2 | 1.9 | 6.5 | 4.3 | g per 100 g protein |
| Histidine | 0.7 | 1.1 | 1.3 | 1.7 | g per 100 g protein |
| Isoleucine | 3.2 | 2.2 | 2.4 | 3.2 | g per 100 g protein |
| Leucine | 3.5 | 3.4 | 4.2 | 5.4 | g per 100 g protein |
| Lysine | 4.8 | 2.9 | 4.5 | 5.5 | g per 100 g protein |
| Methionine | 1.3 | 0.6 | 1.7 | 2.2 | g per 100 g protein |
| Phenylalanine | 1.9 | 2.2 | 2.1 | 2.8 | g per 100 g protein |
| Proline | 1.6 | na | na | na | g per 100 g protein |
| Serine | 2.0 | 2.5 | 3.1 | 2.8 | g per 100 g protein |
| Threonine | 2.5 | 1.9 | 2.5 | 3.1 | g per 100 g protein |
| Tryptophan | na | 0.6 | 0.6 | 0.8 | g per 100 g protein |
| Tyrosine | 2.1 | 1.6 | 1.7 | 2.3 | g per 100 g protein |
| Valine | na | 2.3 | 2.9 | 3.9 | g per 100 g protein |
| Total Crude Protein | 72.0 | 45.0 | 65.0 | 72.0 | g per 100 g |
| Macronutrients comparison | | | | | |
| Moisture | 15 | 11 | 10 | 8 | g per 100 g |
| Total protein | 72 | 46 | 65 | 72 | g per 100 g |
| Crude fat | ND | 1 | 5 | 9 | g per 100 g |
| Ash | 3 | 6 | 20 | 10 | g per 100 g |
| Crude fiber | 9 | 6 | 0 | 0 | g per 100 g | na = not available
ND = not detected (below the detection limit of the method)
*FAO Fisheries Technical Paper - 142, (1986). Retrieved 2015.

Example 3

This example describes general methods for culturing *C. autoethanogenum* and *C. ljungdahlii*. Such methods are also well known in the art.

*C. autoethanogenum* DSM10061 and DSM23693 (a derivate of DSM10061) and *C. ljungdahlii* DSM13528 were sourced from DSMZ (The German Collection of Microorganisms and Cell Cultures, Inhoffenstraße 7 B, 38124 Braunschweig, Germany).

Strains were grown at 37° C. in PETC medium at pH 5.6 using standard anaerobic techniques (Hungate, *Methods Microbiol*, 3B: 117-132, 1969; Wolfe, *Adv Microbiol Physiol*, 6: 107-146, 1971). Fructose (heterotrophic growth) or 30 psi CO-containing steel mill gas (collected from New Zealand Steel site in Glenbrook, NZ; composition: 44% CO, 32% $N_2$, 22% $CO_2$, 2% $H_2$) in the headspace (autotrophic growth) was used as substrate. For solid media, 1.2% bacto agar (BD, Franklin Lakes, N.J. 07417, USA) was added.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgment that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process comprising:
   a. obtaining a gaseous substrate comprising one or more of CO, or $CO_2$, and $H_2$ from an industrial process waste gas, an industrial process off gas, or syngas;
   b. culturing the gaseous substrate in a two reactor system by contacting it with a microorganism, which is an anaerobe, selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides, Thermoanaerobacter kivui*, and mixtures thereof, under fermentation conditions wherein the microorganism dilution rate in the second reactor is higher than the microorganism dilution rate in the first reactor, and the microorganism dilution rate of the second reactor is from about 1/day to about 2/day to maximize production of microbial biomass, and to generate a product selected from the group consisting of acetate, acetic acid, ethanol, 2,3-butanediol, lactic acid, and mixtures thereof, in a fermentation broth;
   c. isolating the biomass from the fermentation broth,
   d. drying the microbial biomass wherein the microbial biomass contains greater than 85% protein by weight on a dry solids basis,
   e. separating at least one product from at least a portion of the fermentation broth.

2. The process of claim 1 wherein the syngas is generated through gasification of coal, refinery residues, biomass, lignocellulosic material, municipal solid waste, industrial solid waste or mixtures thereof.

3. The process of claim 1 wherein the syngas is generated by reforming natural gas.

4. The process of claim 1 wherein the industrial process is ferrous metal products manufacturing, petroleum refining processes, coal gasification, electric power production, carbon black production, ammonia production, methanol production, and coke manufacturing.

5. The process of claim 1, wherein the separation of the at least one product from at least a portion of the fermentation broth is by fractional distillation, evaporation, pervaporation, gas stripping, phase separation, or extractive fermentation.

6. The process of claim 1, wherein the method further comprises reducing the nucleic acid content of the microbial biomass.

7. The process of claim 1, wherein the method further comprises one or more steps selected from the group consisting of sterilizing the microbial biomass and centrifuging the microbial biomass.

8. The process of claim 1, wherein the drying is spray drying or paddle drying.

9. The process of claim 1, wherein the method further comprises combining the microbial biomass with an excipient to produce animal feed.

10. The process of claim 1, wherein the microorganism is selected from the group consisting of *Clostridium autoethanogenum, Clostridium ljungdahlii, Clostridium ragsdalei*, and *Clostridium coskatii*.

11. The process of claim 1, wherein the gaseous substrate comprises CO.

12. The process of claim 1, wherein the gaseous substrate does not comprise methane.

13. The process of claim 9, wherein the animal feed is suitable for feeding to livestock or pets.

14. The process of claim 9, wherein the animal feed is suitable for feeding to one or more of beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents.

15. The process of claim 9, wherein the excipient comprises one or more of a carbohydrate, fiber, fat, protein, vitamin, mineral, water, flavor, sweetener, antioxidant, enzyme, preservative, probiotic, or antibiotic.

16. The process of claim 9, wherein the excipient comprises one or more of alfalfa, animal fat, bakery waste, barley, beet pulp, bermudagrass, blood meal or plasma, brewer's grain, brewer's yeast, bromegrass, buckwheat, canarygrass, canola, casein, citrus pulp, clover, coconut, corn, corn cob, cottonseed, feather meal, fescue, fish meal or solubles, hominy, meat or bone meal, milk, millet, molasses, oats, orchardgrass, peas, peanuts, poultry meal, rice, rye, ryegrass, safflower, sesame, sorghum, soybean, sunflower, timothy, triticale, urea, wheat, whey, or yeast.

* * * * *